United States Patent [19]

Ritson et al.

[11] Patent Number: 4,784,577

[45] Date of Patent: Nov. 15, 1988

[54] PUMP PRESSURE SENSOR

[75] Inventors: Carl Ritson, San Jose, Calif.; Hal C. Danby, Sudbury, England

[73] Assignee: Critikon, Inc., San Jose, Calif.

[21] Appl. No.: 25,300

[22] Filed: Mar. 13, 1987

Related U.S. Application Data

[63] Continuation-in-part of Ser. No. 902,616, Sep. 2, 1986.

[51] Int. Cl.$^4$ .................. F04B 1/06; A61M 31/00; A61B 5/08
[52] U.S. Cl. .................. 417/219; 417/38; 417/63; 417/413; 604/65; 604/131; 604/152; 604/153; 128/722; 73/718
[58] Field of Search .................. 604/65, 118, 121, 151, 604/152, 153, 131; 128/DIG. 1, DIG. 12, DIG. 13, 722, 672, 675; 417/413, 219, 38, 63, 18; 73/718

[56] References Cited

U.S. PATENT DOCUMENTS

| | | | |
|---|---|---|---|
| 3,831,588 | 8/1974 | Rinder | 604/118 |
| 4,236,880 | 12/1980 | Archibald | 604/153 |
| 4,322,201 | 3/1982 | Archibald | 604/152 |
| 4,324,259 | 4/1982 | Wright | 128/722 |

Primary Examiner—C. Fred Rosenbaum
Assistant Examiner—Gene B. Kartchner
Attorney, Agent, or Firm—William B. Walker

[57] ABSTRACT

A back pressure sensor comprising a flexible beam having a pivot end with a pivot pin and a drive connector end with a means for engaging a pump drive. A pump actuator is connected to the flexible beam at a position intermediate the ends and connects with a positive displacement pumping member. A sensor beam is attached to the flexible beam at a connecting point spaced from said pivot end. A first capacitor plate is mounted on the flexible beam at a point which is spaced from the connecting point. A second capacitor plate is mounted on the sensor beam in a position facing and spaced apart from the first capacitor plate at a distance therefrom which permits formation of a capacitance coupling therebetween. The back pressure sensor is particularly advantageous for use with positive displacement pumps such as diaphragm pumps, peristaltic pumps and piston pumps used in parenteral solution delivery systems where substantially increases in back pressure present a hazard to the patient to which liquid is being infused.

19 Claims, 11 Drawing Sheets

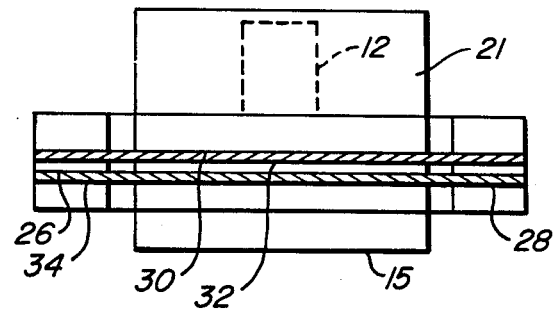

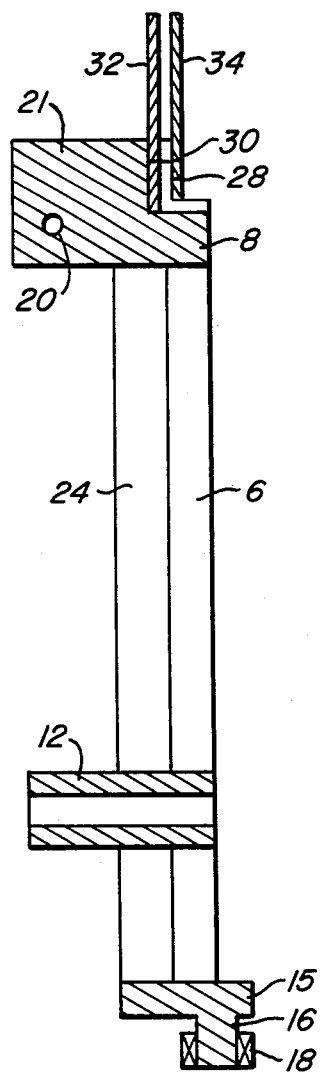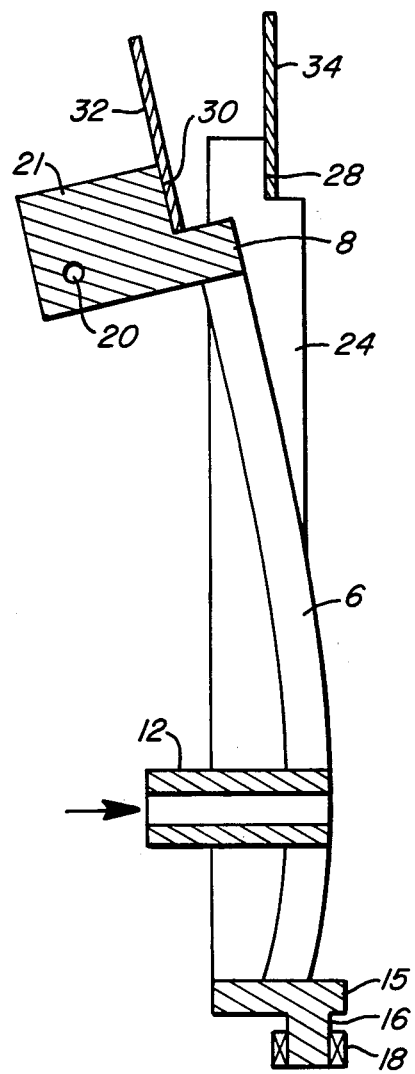
FIG._4.  FIG._5.

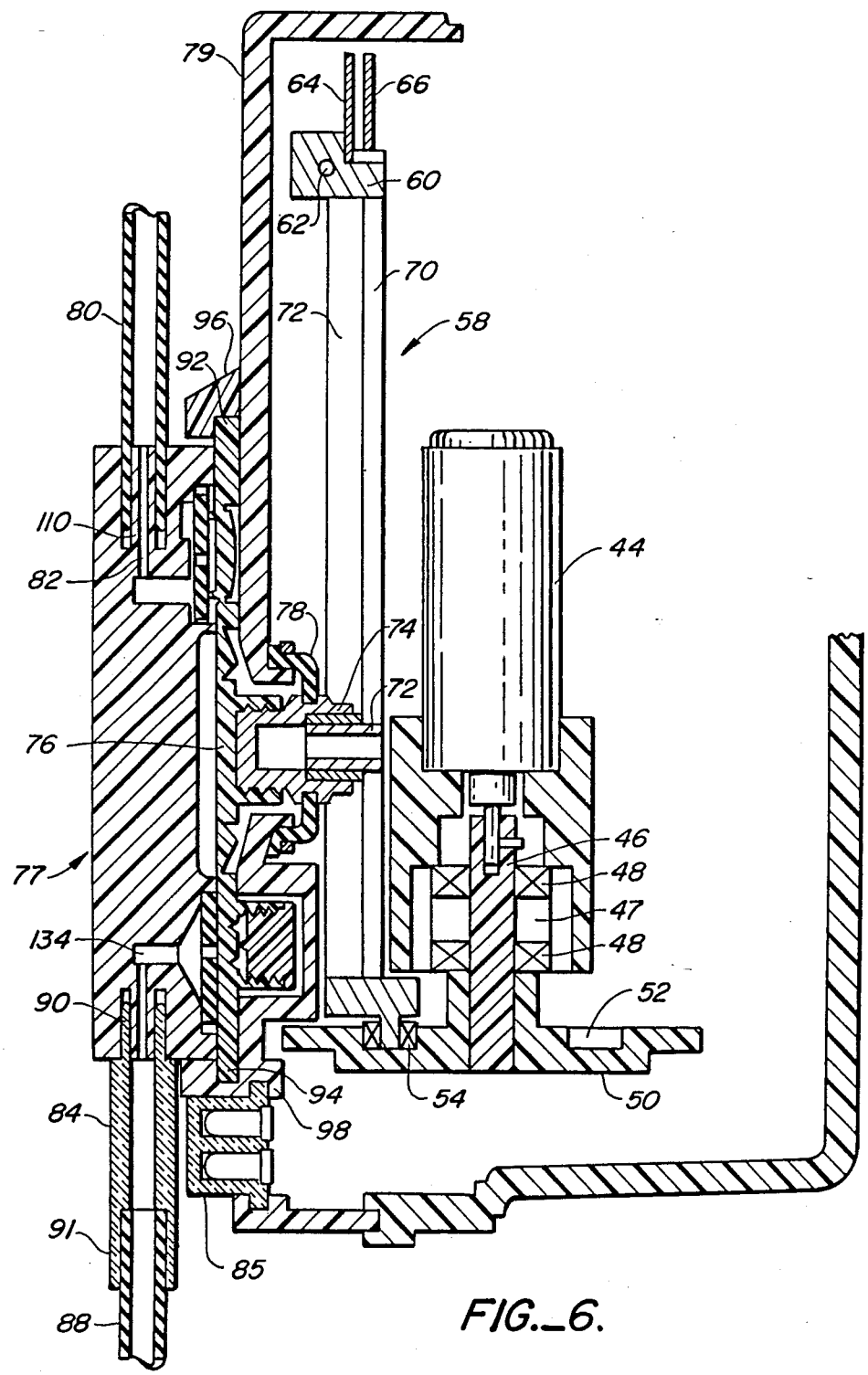
FIG._6.

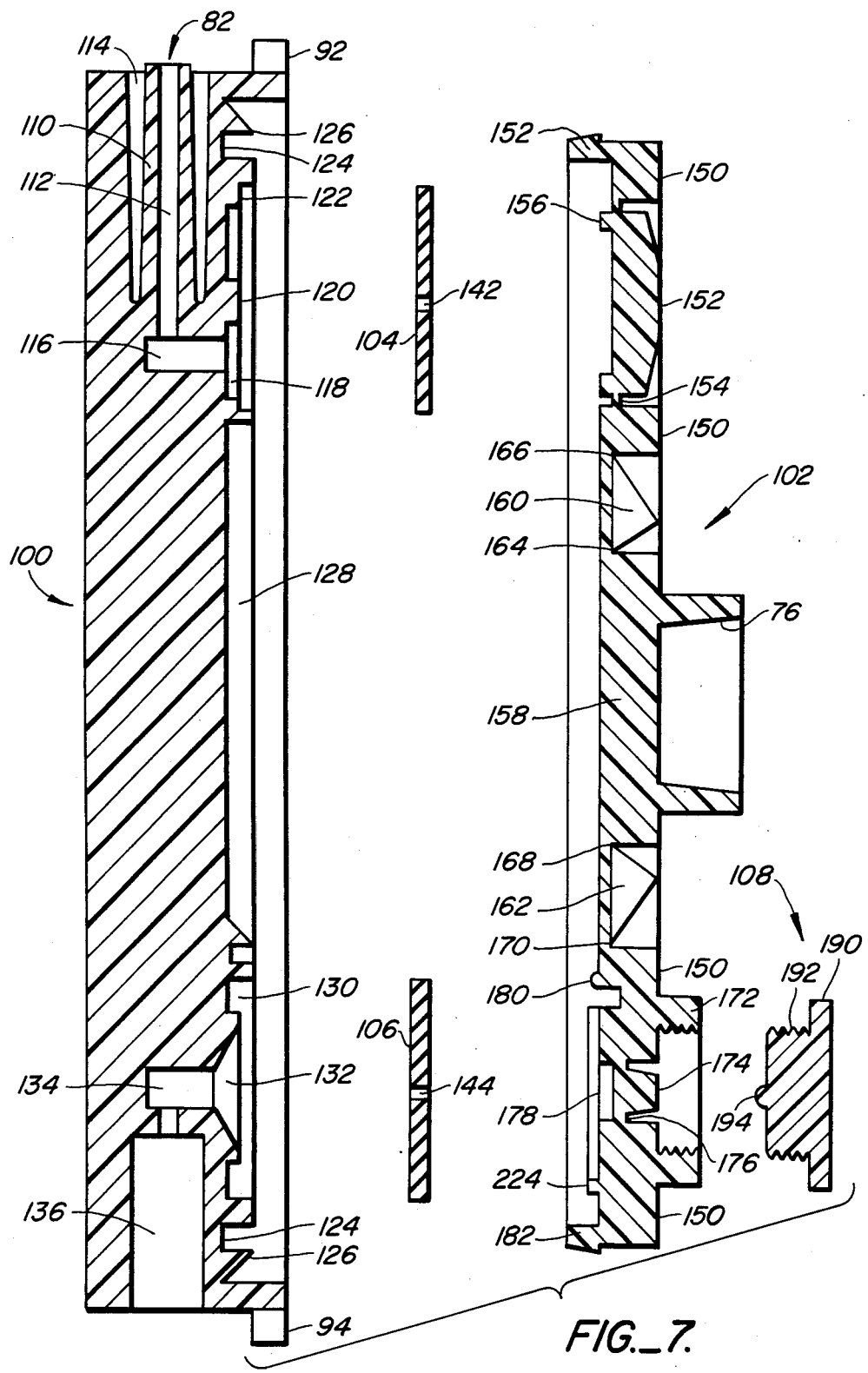
FIG._7.

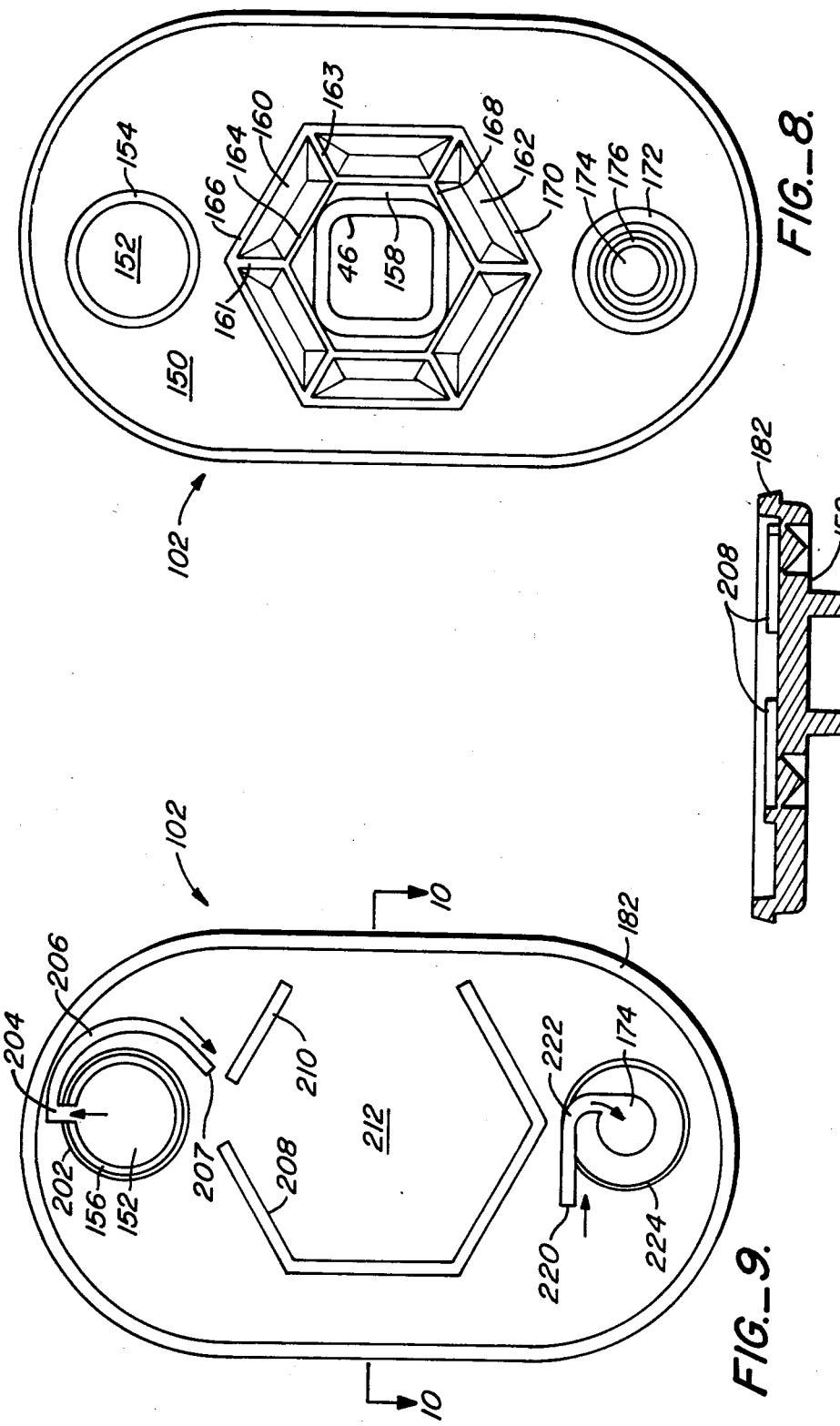

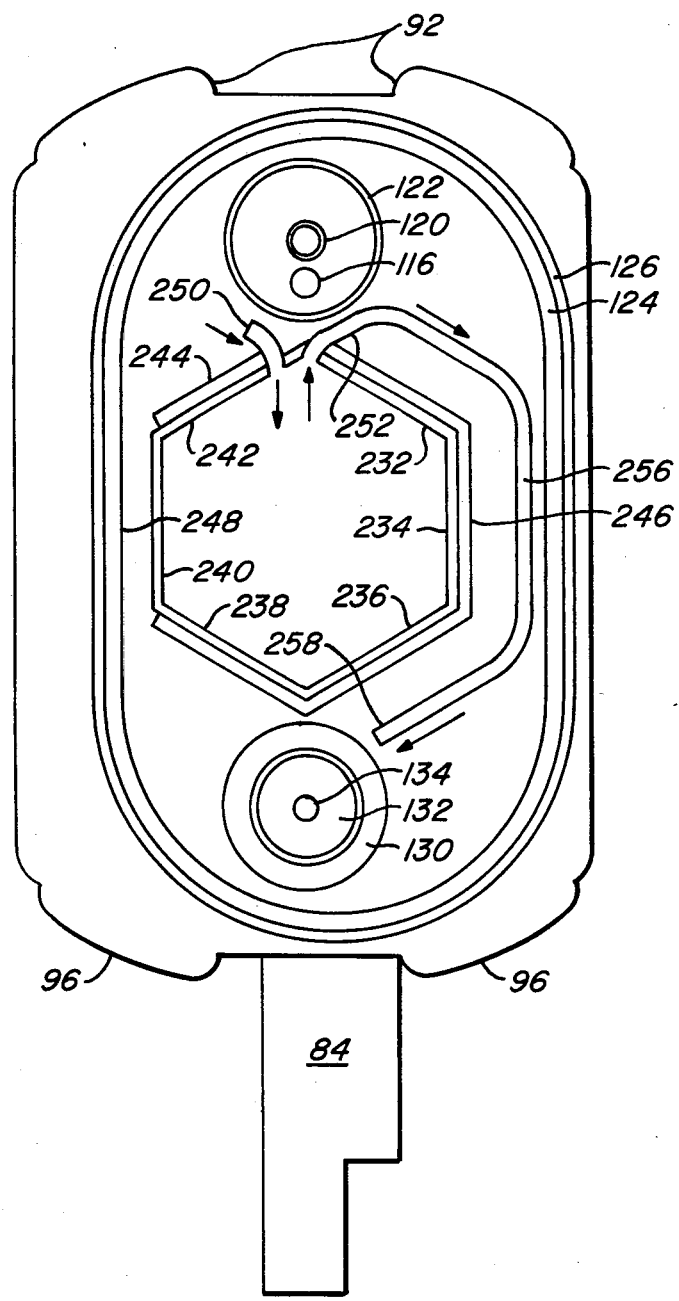
FIG._11.

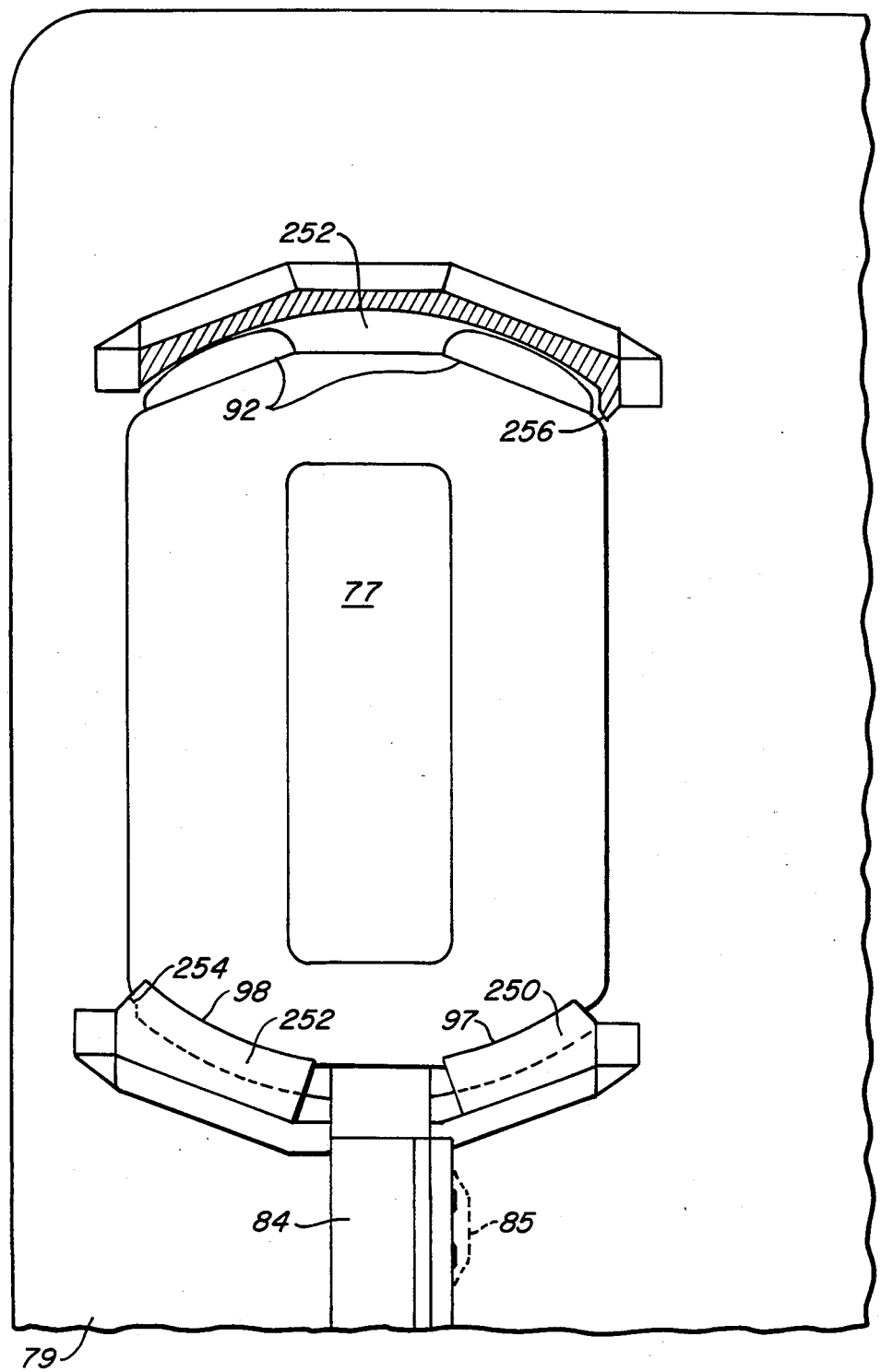
FIG._12.

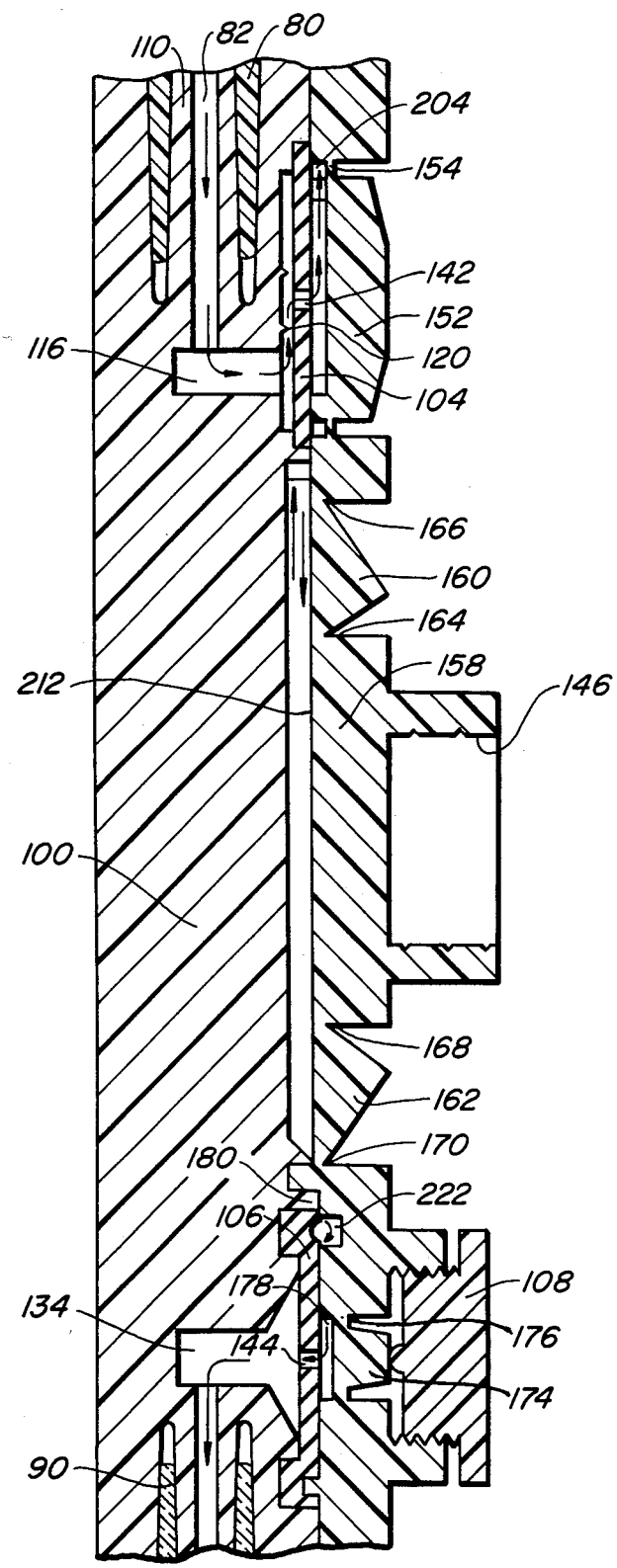
FIG._13.

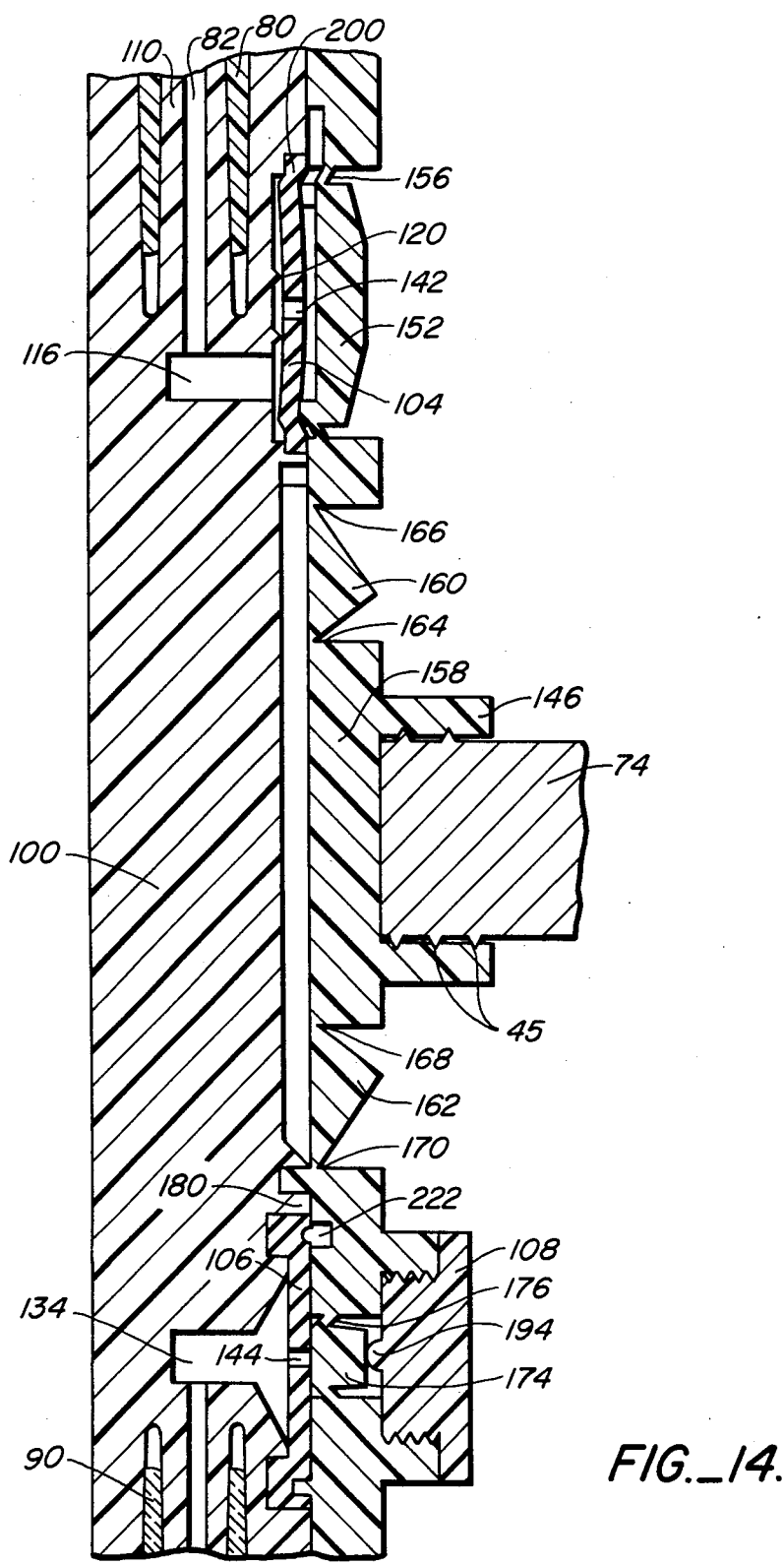
FIG._14.

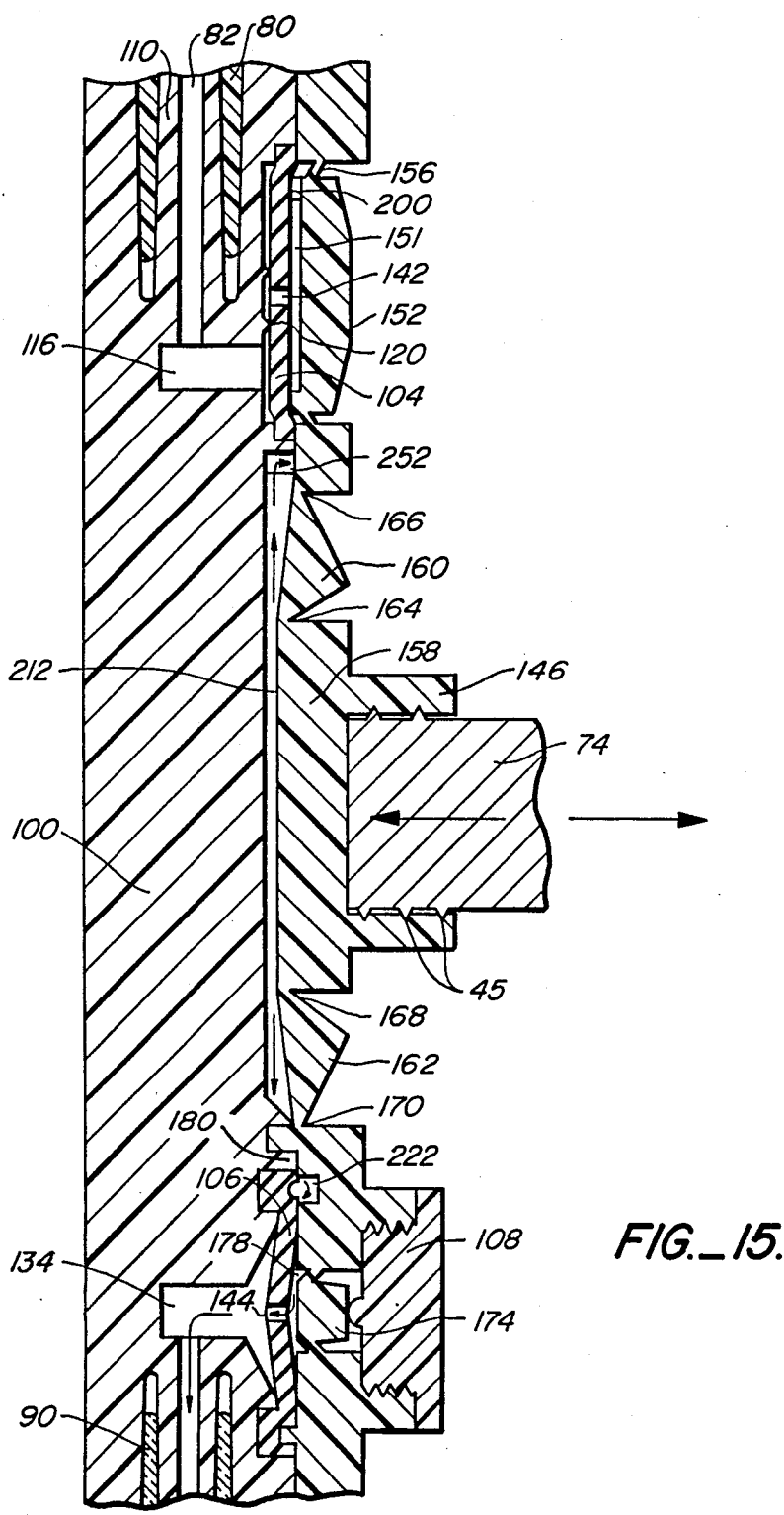
FIG._15.

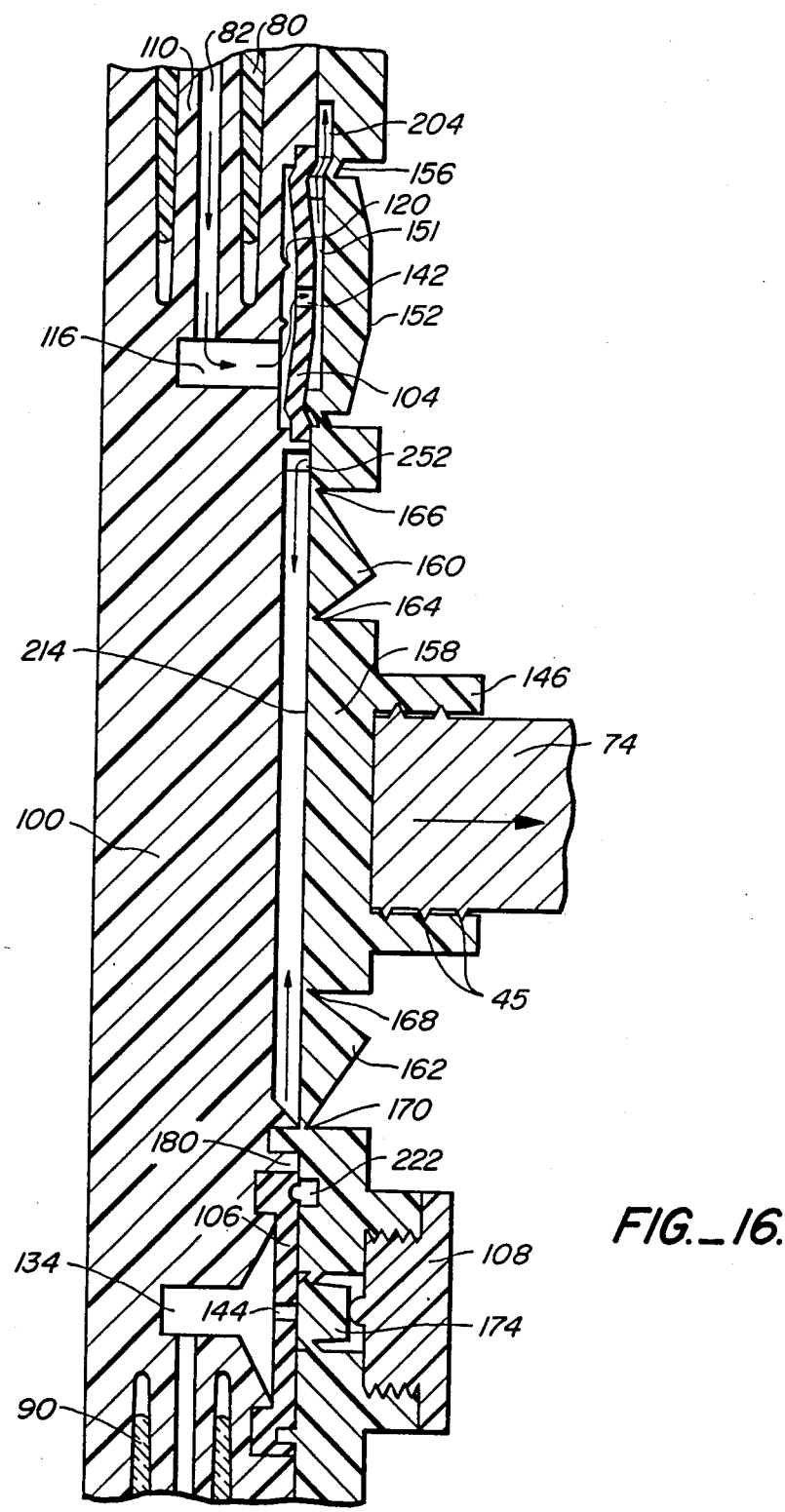
FIG._16.

PUMP PRESSURE SENSOR

RELATIONSHIP TO COPENDING APPLICATION

This application is a continuation-in-part of copending application Ser. No. 902,616 filed Sept. 2, 1986.

FIELD OF THE INVENTION

This invention relates to improvements in fluid delivery systems, and in particular to parenteral solution or intravenous pumps. Most particularly this invention relates to a pressure sensor which monitors the back pressure or pumping pressure of liquid pumping systems.

BACKGROUND OF THE INVENTION

Pumping systems for the delivery of fluids intravenously or intra arterially are well known in the prior art and are in widespread daily use in hospitals throughout the world. These systems are commonly used for the intravenous or intra arterial delivery of such fluids as glucose solutions and blood plasma, and for the delivery of drugs, all at controlled delivery rates based on the patient's need, and in the case of drugs, the drug concentration being delivered.

Pumping systems offer advantages of mobility and positive control of flow rates by pump motor control. The prior art pumps include both peristaltic pumps and other positive displacement pumps. Both have the disadvantage of possible patient injury if an obstruction prevents free flow of liquid to the patient. Pumping pressure then increases until the obstruction clears or the equipment fails. The high pressure present upon sudden clearance of the obstruction can cause serious injury to the patient.

DESCRIPTION OF THE PRIOR ART

U.S. Pat. No. 3,739,943 describes a parenteral solution pump with a pressure monitor.

Pumps which squeeze or apply a positive fluid displacement member against a tube or pumping chamber segments and which control fluid flow to and from the pumping chamber with further positively controlled tube pinching members including peristaltic pumps and similar systems are described in U.S. Pat. Nos. 4,199,307, 4,273,121 4,290,346, and 4,515,589, for example. A combination of a peristaltic pump and a back pressure monitor is described in U.S. Pat. No. 4,460,355.

Syringe pumps are described in U.S. Pat. No. 3,739,943 using a disposable hypodermic syringe as the pumping chamber and with a back pressure monitor. A syringe pump is also disclosed in U.S. Pat. No. 4,515,591.

A piston pump with a radially segmented spring element is described in U.S. Pat. No. 4,276,004. Piston pumps with the piston or equivalent displacement member covered with an elastic rubber barrier to isolate the pump chamber from the drive members are described in U.S. Pat. Nos. 4,140,118, 4,336,800, 4,453,931, 4,453,932, 4,457,753, and 4,519,732. Most piston pumps have inlet and outlet check valves. One or both of the inlet and outlet check valves in U.S. Pat. Nos. 4,126,132 and 4,468,222 are open during a fluid priming step prior to loading the pumping cassette into the operating housing, and are automatically activated into an operational position by the insertion of the cassette into the housing. In U.S. Pat. No. 4,468,222, the disposable cassette comprises an elastic diaphragm defining one wall of the pumping chamber and inlet and outlet valve members having a one piece molded construction.

Diaphragm pumps usually have resilient diaphragm members which are connected to a drive member, and are usually combined with inlet and outlet check valves as described in U.S. Pat. Nos. 2,812,716 and 2,954,738. Diaphragm pumps comprising concentric cylindrical segments isolated from the pumping chamber with a rubber diaphragm are described in U.S. Pat. No. 1,923,970 and 3,200,757.

SUMMARY OF THE INVENTION

One aspect of this invention is a pump-pressure sensor combination comprising a pumping chamber for containing liquid to be pumped, liquid displacement means including a positive displacement member for reducing the volume in the pumping chamber and thereby expelling liquid from the pumping chamber, and a back pressure sensor for monitoring the pressure developed in the pumping chamber during displacement action of the liquid displacement means. The positive displacement member is positioned to engage the pumping chamber to effect displacement of liquid.

The back pressure sensor comprises a flexible beam having a pivot end and a drive connector end. A pivot means is positioned at the pivot end thereof, and a connector means is positioned at the connector end thereof for engaging a pump drive. A pump actuator means is positioned on the flexible beam at a position intermediate the ends for engaging the positive displacement member. A sensor beam is attached to the flexible beam at a connecting point spaced from said pivot point. A first capacitor plate is mounted on the flexible beam at a point which is spaced from the connecting point. A second capacitor plate is mounted on the sensor beam facing the first capacitor plate and spaced apart therefrom a distance therefrom which permits formation of a capacitance coupling therebetween. In the preferred back pressure sensor of this invention, the connecting point of the flexible beam is adjacent the drive connector end.

BRIEF DESCRIPTION OF THE DRAWINGS

FIG. 1 is a front view of the sensor beam with the capacitor plates shown in dotted line representation.

FIG. 2 is a side view of the sensor beam shown in FIG. 2 with the capacitor plates shown in solid line representation.

FIG. 3 is a top view of the sensor beam shown in FIG. 2 with the capacitor plates shown in solid line representation.

FIG. 4 is a cross-sectional view of the sensor beam, taken along the line 4—4 of FIG. 1 in the unflexed or relaxed position.

FIG. 5 is a cross-sectional view of the sensor beam of FIG. 4 as flexed under the influence of back pressure.

FIG. 6 is a partial cross-sectional representation of a pump combined with the back pressure sensor of this invention.

FIG. 7 is an exploded cross-sectional representation of one embodiment of the disposable cassette elements prior to assembly.

FIG. 8 is a back view of the back plate shown in FIG. 7.

FIG. 9 is a front view of the back plate shown in FIG. 8.

FIG. 10 is a cross-sectional view of the back plate shown in FIG. 9, taken along the line 10—10.

FIG. 11 is a back view of the front closure plate shown in FIG. 7.

FIG. 12 is a front view of front closure plate shown in FIG. 11.

FIG. 13 is a partial cross-sectional view of the cassette assembly showing the pump diaphragm and inactive check valves during priming.

FIG. 14 is a partial cross-sectional view of the cassette assembly of FIG. 13 showing the check valves after activation.

FIG. 15 is a partial cross-sectional view of the installed cassette assembly of FIG. 13 during the output phase of the pumping cycle.

FIG. 16 is a partial cross-sectional view of the installed cassette assembly of FIG. 13 during the filling phase of the pumping cycle.

DETAILED DESCRIPTION OF THE INVENTION

The back pressure sensor is a highly effective system for continuously monitoring the pressure in a pumping chamber during the positive displacement phase of the pumping cycle. It can be easily incorporated into any positive displacement pumping system where back pressure monitoring is important and particularly where excessive back pressure creates a serious hazard as with parenteral solution pumping systems. It is particularly advantageous for use in parenteral solution delivery pumping systems such as are described in our copending application Ser. No. 902,616 filed Sept. 2, 1986, the entire contents of which are hereby incorporated by reference in their entirety.

FIG. 1 shows a frontal view of one embodiment of the sensor assembly of this invention, and FIG. 2 and FIG. 3 are the side and top views thereof, respectively. The key to this assembly are one or more flexible beams which are flexed by back pressure and one or more sensor beams which remain unflexed. The distance between capacitor plates mounted on the flexible and sensor beams changes as the flexible beams are flexed. The change in capacitance produced by the change in capacitor plate spacing is functionally related to the amount of back pressure, and by monitoring the capacitance changes during the pumping cycle, data about the back pressure is obtained. The device can be used with conventional control systems which will give an alarm and/or shut down the pumping system. These can be activated when and if the capacitance (and back pressure) reaches a value predetermined to indicate a hazardous condition.

The sensor assembly 2 comprises, in the view shown in FIG. 1, a flexible left beam 4 and a flexible right beam 6 joined at their pivot ends by a pivot end crossbar 8. Beams 4 and 6 are joined at an intermediate position by pump actuator crossbar 10 having a pumping actuator projection 12 (FIG. 2 and FIG. 3) mounted thereon. The drive connector end of the beams 4 and 6 are joined by a lower drive end crossbar 14 having a frontal projection 15 upon which drive bearing mount 16 is positioned. Drive bearing 18 is supported on drive bearing mount 16. Movement of the drive bearing 18 pivots the beam assembly around pivot 20 (FIG. 2) in the rear extension 21 of the crossbar 8. This pivotal motion is translated to a linear pump actuating motion by projection 12, by which it is transmitted to a positive displacement pumping member such as a piston, compression member or diaphragm of a pump.

Left sensor beam 22 and right sensor beam 24 are securely mounted on the ends of the crossbar 14 and extend parallel to the flexible beams 4 and 6 along the sides thereof. The mounting is fixed and rotation of the sensor beam about the mounting position is prevented. Preferably, the flexible beam and sensor beams are made of metal or a durable organic polymer and are joined as shown by a short connecting portion integral to the beams.

The terminal unsupported ends of the sensor beams 22 and 24 have capacitor plate support surfaces 26 and 28 thereon. The front of the crossbar 8 also has a capacitor plate support surface 30 thereon. The relative position of the capacitor plates in the front view is shown by a dotted line representation, leaving the support surfaces unobscured for clarity.

The relative orientations of the mounted flexible beam capacitor plate 32 and sensor beam capacitor plate 4 are shown more clearly in FIG. 2 and FIG. 3 where the parallel capacitor plates are shown in solid line representations. The sensor beam capacitor plate 34 is shown mounted in front of the flexible beam capacitor plate 32, being supported by the supporting surfaces 26 and 28, and extends between the supporting surfaces 26 and 28 like a crossbar. The flexible beam capacitor plate 32 is shown positioned behind the capacitor plate 34, mounted on the single support surface 30 of the pivot crossbar 8. The distance between the parallel plates 32 and 34 is selected to provide an optimum capacitance coupling.

FIG. 4 is a cross-sectional view of the sensor beam assembly, taken along the line 4—4 of FIG. 1 in the unflexed or relaxed position, and FIG. 5 is a cross-sectional view of the sensor beam with the flexible beam assembly flexed under the influence of back pressure. The crossbar 8 and integral pivot ends of the flexible beams 4 and 6 are mounted for pivotal movement around the pivot 20. The lower end or driver crossbar 14 is driven through a reciprocating path by reciprocal movement of the drive bearing 18 and bearing support 16. As the bearing 18 is moved to the left, the pump actuator 12 is moves to the left, transferring the movement to a pump displacement element (FIG. 6). Back pressure from the pumping chamber is realized by resistance to the movement of the actuator 12 to the left, that is, the pressure bears in the direction of the arrow against the actuator 12 and the corresponding connecting point of the flexible beams 4 and 6. Beam flexure between the flexible beam ends shown in an exaggerated aspect in FIG. 5 thus occurs. The resulting curve of beams 4 and 6 displace the crossbar 30 and capacitor plate 32 mounted thereto to the left from the stationary capacitor plate 34, increasing the distance therebetween, and lowering the capacitance between the plates. The capacitor plates 32 and 34 can be connected to a pump control system such as is described in concurrently filed United States patent application number (CRIK-103) filed concurrently herewith, the entire contents of which are hereby incorporated by reference. This pump control system provides a technique for measuring cassette compliance and depliance. The measured cassette compliance or depliance is used to determine the actual volume of fluid which was pumped during a pumping cycle, and this actual value is then used to calibrate the pumping rate for precisely controlling the fluid delivery. Because the back pressure system is coupled directly to the drive assembly, the back pressure is reflected by capacitor plate distances throughout the pumping cycle. Therefore, an immediate signal is obtainable at any part of the cycle when the back pressure exceeds a level which has been predetermined to be hazardous. This alarm signal can also be used to shut off the system, sound an alarm or institute any other action desired.

This system has been shown with two pairs of beams and two capacitor plates. It will be readily apparent to a person skilled in the art that a single flexible beam and a single sensor beam, each bearing a capacitor plate can be used. Alternatively, a pair of capacitor plates can be mounted on the pivotal end of the flexible beam, with the sensor beam capacitor positioned therebetween. In this alternate design, readings can be obtained from each adjacent pair of plates and compared or manipulated to provide an increased sensitivity, if desired.

FIG. 6 is a partial cross-sectional representation of one embodiment of a pump-pressure sensor combination of this invention. The DC motor 44 has a drive shaft 46 supported by bearings 48 with sprag clutch 47, the distal end of the drive shaft 46 being connected to a drive wheel 50. The drive wheel 50 has a cam groove 52 in the back face thereof engaged by the cam follower bearing 54 attached to the drive end of the sensor beam assembly 58. The opposite pivot end 60 of the drive beam 58 is mounted for pivotal movement around pin 62. The capacitor plates 64 and 66 are supported on the ends of the respective flexible beam 68 and sensor beam 70 as shown in detail in FIGS. 1-5.

The drive actuator connector 72 is attached to a barbed, self-threading connector 74 (shown in detail in FIGS. 13-16) and joined to a central portion of the flexible drive beam 70. The barbed, self-threading connector 74 engages a female receptor 76 integral with the central diaphragm plate on the back plate of the pump cassette 77. The flexible plate diaphragm is described in our copending application Ser. No. 799,235 filed Nov. 18, 1985, the entire contents of which are hereby incorporated by reference in its entirety. The flexible plate diaphragm will be shown in greater detail hereinafter.

The distance of the contact point of the cam groove 52 and the cam follower 54 from the central axis of the drive shaft 46 varies as the drive shaft rotates, translating the rotary motion of the drive shaft to a reciprocating displacement of the cam follower drive bearing 54 and cassette drive connector 74. The drive connector 76 thus imparts a reciprocating motion to the diaphragm plate of which the female drive connector 74 is a part. A annular flexible splash shield 78 is secured to the male drive connector and the surrounding edges of the housing 79 to prevent liquid contaminants from reaching the interior of the housing 79.

Inlet tubing 80 from a liquid source (not shown) is secured to a tubing connector inlet 82 of the cassette 77. An optional air-in-line detector component 84 of this combination extends from connecting portion 90 in the bottom of the cassette 77 below the outlet valve cavity 134, communicating therewith. It faces a light source-detector array 85. The air-in-line detector is described in detail in our copending application titled AIR IN LINE DETECTOR by Hal C. Danby and Carl Ritson, (116.0139), and the contents thereof are hereby incorporated in this application by reference in their entirety. Outlet tubing 88 extending to the patient is secured to a tubing connector outlet 91 of the cassette.

The cassette 77 is secured to the housing 79 by tabs or ears 92 and 94 extending from the cassette 77 into corresponding grooves defined by retention projections 96 and 98 extending from the front of the housing.

FIG. 7 is an exploded cross-sectional representation of one embodiment of the five disposable cassette elements prior to assembly.

The disposable pump cassette 77 comprises a front plate 100, back plate 102, resilient inlet check valve washer 104, resilient outlet check valve washer 106 and outlet check valve engaging knob 108. The front plate 100 has an inlet tube connector 82 consisting of a nipple extension 110 with an inlet fluid passageway 112 for entering and expanding the tubing 80 (FIG. 6), and a surrounding annular recess 114 for receiving the tubing wall as the tubing is slipped over the nipple 110. The inlet passageway 112 communicates with the inlet check valve inlet 116 and annular inlet check valve cavity 118. The inlet check valve cavity 118 surrounds the stationary valve seat element 120. An circular inlet check valve washer receptor is defined by annular rim 122 for supporting the edges of the check valve washer 104.

Swage joint groove 124 and swage projection 126 extend completely around the back face edge of the front plate 100. Pumping cavity 128 is positioned on the back face of the front plate 100 between the inlet check valve elements and the outlet check valve elements.

The outlet check valve elements of the front plate include the outlet check valve washer receptor defined by the annular groove 130 which surrounds the conical outlet check valve cavity 132. The check valve outlet 134 communicates with the cavity 132 and the receptor 136 for the air-in-line detector 84 (shown in FIG. 6).

The inlet check valve washer 104 is a resilient, elastic material in the form of a disk with a central flow passageway 142. The outlet check valve washer 106 is a resilient, elastic material in the form of a disk with a central flow passageway 144.

The back check valve plate 102 is also of unitary construction and includes the check valve activation elements, segmented pump diaphragm, and pump drive connector element. Whereas the front plate 100 is made of rigid plastic, the back plate is made of a plastic such as polyethylene which is essentially rigid in thickened portions and flexible and extendable in thinned connecting portions.

The thickened, inflexible back plate 150 surrounds and is connected to the thickened, inflexible inlet check valve activation disk 152 by the flexible, extendable annular connecting web 154. The front face of the disk 152 has an annular raised ridge 156. The pump diaphragm comprises an inflexible central plate 158 integral with the female pump drive receptor 76, surrounded by the inflexible back plate 150 and connected thereto by rigid, hinged pump segments 160 and 162. Pump segment 160 is connected to the central plate 158 by thinned, flexible hinge portion 164 and to the surrounding back plate 150 by thinned, flexible hinge portion 166. Pump segment 162 is connected to central plate 158 by thinned, flexible hinge portion 168 and to the back plate 150 by thinned, flexible hinge portion 170. Outlet check valve activation element 174 is connected to the bottom edge of the knob receptor 172 by a thinned, flexible, extendable annular web 176. The circular outlet check valve cavity is defined by circular recess 178 in the front, central face of the disk 174. Annular raised ridge 180 extending from the front face of the outlet check valve portion of the plate 150 secures the outlet check valve disk 106 in place when the front and back pieces are joined. Swage joint ridge element 182 extends from the front face of the periphery of the back plate 102.

Outlet check valve activation knob 108 has a grip flange portion 190, a threaded cylindrical portion 192 for engaging the threaded receptor 172, and an axially concentric projection 194 for engaging the opposing surface of the outlet check valve disk 174 when advanced against it.

FIG. 8 is a back view of the back plate shown in FIG. 7, FIG. 9 is a front view of the back plate, and FIG. 10 is a cross-sectional view of the back plate shown in FIG. 9, taken along the line B—B. In FIG. 8 the overall configuration of the check valves and diaphragm shown in cross-section in FIG. 7 can be seen. The rigid hexagonal diaphragm plate 158, on which the drive receptor 46 is supported, is joined to the surrounding rigid back plate 150 by six rigid trapezoidal plates, the optimum configuration for a pump having the size suitable for parenteral solution delivery. Each trapezoidal plate is joined to the back plate by a thinned, flexible, yieldable hinge such as 166 and 170, and is joined to the hexagonal diaphragm plate 158 by a thinned, flexible, yieldable hinge such as 164 and 168. The adjacent edges of adjacent trapezoidal plates are joined by thinned, flexible, yieldable hinges such as 161 and 163, for example. This pattern is repeated with each trapezoidal plate.

The preferred, flexible diaphragm member has at least three inflexible diaphragm plates with edges in a common plane, each diaphragm plate having at least two straight diaphragm plate hinge edges. Each diaphragm plate hinge edge is adjacent to and aligned with a second diaphragm plate hinge edge of an adjacent diaphragm plate. The adjacent edges of each diaphragm plate hinge edge and second diaphragm plate hinge edge are attached together by a flexible hinge strip. Optimally, when the first array of plates comprises at least three identical plates having identical edges, the respective identical edges thereof are positioned equal distant from the axial center of symmetry. Additionally, the flexible member can include a central plate as shown in FIG. 8, the axial center of the center plate being at the axial center of symmetry. The center plate optimally has straight plate edges having the same length, and the plates include an array of plates hingingly connected to the straight sides of the center plate. Each plate in the array of plates then has a straight center plate hinge edge positioned adjacent to and aligned with a center plate edge and hingingly connected at the center plate edge by a flexible hinge strip.

In the embodiment illustrated in the drawings, a total of six plates are assembled in a symmetrical array around the axial center. It will be readily apparent that the number of plates can be selected as desired, a minimum of three plates being required for operation in the intended manner. The flexible hinge elements are distorted by both flexure and stretching during the movement of the diaphragm element, and as the number of segments are reduced, greater energy is expended to effect flexure. Stretch distortion of the hinge increases toward the center of the diaphragm, and this distortion is increased by reducing the number of plates. Increasing the number of segments increases the flexible hinge area and reduces the stretching required for diaphragm movement, both reducing energy requirements. Increasing the hinge width and reducing the thickness of the hinge also increases hinge flexibility and elasticity, further reducing energy requirements. However, increasing the number of plates, increasing the relative hinge area and reducing the hinge thickness increases non-linear pumping errors.

An important achievement of the flexible plate diaphragm is the reduction of pumping volume variations which are a function of liquid pressure. Liquid pressure rising in the pumping chamber during a positive pumping stroke and falling during the filling stroke tends to stretch the diaphragm, increasing or decreasing the volume of the pumping chamber, and introducing a non-linear variable in the liquid volume output or input per stroke. The volume displaced during a positive stroke is thus less than would be calculated by simple displacement, and the volume filled during a filling stroke is less than would be calculated by a simple displacement calculation. Because the degree of distortion is a function of the varying pumping chamber pressures, which is in turn, a function of the pumping rate and outlet valve and line back-pressure, this type of distortion cannot be adequately compensated by microcomputer control adjustments and seriously impairs pumping accuracy.

This effect is very pronounced with the flexible diaphragm pumps known prior to this invention. Piston pumps, while avoiding this problem, use more power and require a more complex construction to prevent leakage from the pumping chamber around the piston.

With the plate diaphragm construction of this invention, however, the increased pressure in the pumping chamber does not significantly flex the plate elements, and a more linear relationship between displacement and delivered volume is achieved. With the hinged plate diaphragm of this invention, diaphragm flexure is resisted by the relatively inflexible plates. Only the hinge areas will flex. Thus, the areas subject to flexure are minimized, consistent with the designed power and pressure restraints of a portable, battery operated unit, for example. The diaphragm of FIG. 8, having a central plate and six equal segments, represents a studied compromise of these factors, and is believed to represent a preferred configuration for use with the pump configuration for parenteral solution delivery shown in the drawings.

The plate bearing the flexible plate components and the individual plate element of the diaphragm are preferably relatively rigid to achieve maximum accuracy. This can be achieved by bonding rigid plate elements to a flexible sheet. For example, a relatively rigid polymer can be bonded to a flexible, elastic polymer, combining the rigidity and flexibility desired. In a preferred embodiment of this invention, elements of the front plate bearing the hinged plate diaphragm are formed from a single, homogeneous sheet of plastic. Rigidity is achieved by thickness and flexibility by thinness. Polyolefin plastics such as polyethylene can be used for this construction, for example. In this embodiment, the rigid plates and the flexible hinges are integral parts of a single unit. Corresponding check valve elements can be similarly formed in same sheet of plastic. The back plate can be made of a suitable rigid plastic such as ABS polymer.

Referring to FIG. 9 and FIG. 10, the front surface of the back plate 102 is shown. Within the swage ridge 182 extending around the periphery of the back plate are positioned the check valves 152 and 174 and the grooves and ridges which together with the corresponding grooves and ridges of the front plate form the valve and pumping cavities and fluid flow passageways in the cassette. The inlet check valve face 152 is surrounded by circular ridge 156 which presses the inlet check valve disk 104 (FIG. 7) against the edge of the inlet check valve disk receptor 122 of the front plate. This is surrounded by a circular liquid flow channel groove 202 leading to inlet channels 204 and 206. The inlet channel 206 leads toward the pumping chamber defined by the ridges 208 and 210 surrounding the inner surface 212 of the pump diaphragm. The fluid is then directed from the pumping chamber by a channel 252 and 256 in the back side of the front plate (FIG. 11 described hereinafter) to the inlet 220 of the outlet check valve passageway 222 leading to the outlet check valve chamber 174. The ridge 224 surrounding the check valve chamber 174 presses the outlet check valve disk 106 (FIG. 6) against the edge of the outlet check valve receptor 130 of the front plate.

FIG. 11 is a back view of the front closure plate shown in FIG. 6. The flow passageways in the cassette are formed by a pattern of aligned grooves or channels in the back side of the front closure plate shown in FIG. 11 and the corresponding, engaging front surface of the back plate shown in FIG. 9. The grooves or channels, together with the flat opposing surface of the opposite plate, define enclosed passageways, and references to features shown in FIG. 9 and in FIG. 11 are made in the following description.

The four tabs or mounting flanges 92 and 96 are positioned with one at each corner of the cassette. The swage groove 124 and swage ridge 126 extend around the entire periphery of the front plate. The circular configuration of the inlet check valve structure with inlet passageway 116 and the concentric valve seat 120 and check valve disk receptor 122 are positioned at the upper portion of the front plate positioned to oppose the respective elements of the back plate. The valve seat 120 comprises a raised circular ridge for abutting the inlet check valve washer or diaphragm 104. The outlet check valve elements are concentric. The inlet passageway 134, valve cavity defining cone 132 and the outlet check valve disk receptor 130 are formed in the back surface of the front plate.

The perimeter of the hexagonal diaphragm pump chamber 230 is defined by six sloped edge surfaces 232, 234, 236, 238, 240 and 242. Fluid is further confined within the pump chamber by engaging ridges and grooves on five sides of the pump chamber, parallel to the sloped edge surfaces, and positioned adjacent to the sloped surfaces exterior to the pump chamber. Fluid retention groove 244 is positioned to engage the corresponding fluid retention ridge 210 (FIG. 9). Fluid retention groove 246 extending around four sides of the hexagon is positioned to engage the corresponding fluid retention ridge 208. The close proximity of the pressure swage seal of the edge 248 closely adjacent to and bordering the sixth side 240 of the sloped edge surface provides an effective fluid retention barrier on the sixth side of the pump chamber hexagon.

The pump chamber inlet groove 250 is positioned at the inlet end of the cassette to communicate with the end 207 of the inlet groove 206, for direction of fluid flow from the inlet check valve chamber directly to the pumping chamber. The pump outlet groove 252 is positioned to communicate with the pumping chamber to provide an outlet for the liquid expressed thereby. It communicates with the groove 256 which directs fluid flow to the vicinity of the outlet check valve at the outlet end of the cassette. The outlet end 258 of the fluid outflow passageway 256 communicates with the inlet end 220 of the outlet check valve inlet passageway 222 (FIG. 9). The outlet check valve cavity 174 communicates with the inlet passageway of the air-in-line detector body 84.

FIG. 12 is a partial, fragmented view of the disposable cassette of this invention mounted on the motor housing. The mounting tabs or ears 92 and 94 on the front plate (FIG. 11) are engaged with mounting grooves 250 and 252 (shown as dotted lines) defined by the mounting flanges 97 and 98 by clockwise rotation of the cassette 77. The rotation is terminated by the abutment of the tabs with the ends of the groove, 254 and 256. The drive element 74 (FIG. 6) is fixed against rotation about its axis. Rotation of the cassette to engage the tabs 92 and 94 with the mounting flanges 97 and 98 threads the receptor 46 onto the barbs or self-threading screw threads 45 on the surface of the drive element 74.

FIG. 13 is a partial cross-sectional view of the cassette assembly showing the pump diaphragm and inactive check valves during priming, and FIG. 14 is a view of the cassette assembly showing the check valves after activation. Initially, the knob 108 is rotated to press the element 174 against the diaphragm disk 106 to activate the check valve, the position shown in FIG. 14. This closes the outlet valve, and in this position, the pump cassette can perform the functions of a traditional roller clamp, preventing fluid flow through the system until desired. After connecting the inlet tubing 80 to the inlet tubing nipple 110 and to the liquid source, and after connecting the outlet tubing 88 (FIG. 6) to the system, the outlet check valve is deactivated (opened) by rotating the knob 108 to the position shown in FIG. 13. Liquid then flows from the source through the inlet tubing 80, inlet passageway 82 and into the inlet check valve inlet 116. The inlet check valve washer or diaphragm 104 is spaced from the seat 120 of the inlet check valve, and fluid passes between the ridge 120 and the opposing surface of the inlet check valve diaphragm and through the central opening 142 of the check valve diaphragm. The fluid then passes across the face of the inlet check valve actuator and to the outlet passageway 204 (FIG. 9). The fluid is then directed to the diaphragm pump chamber, displacing air in the pump chamber until it is filled with fluid. The fluid then continues to pass through passageways 252 and 256 (FIG. 11) until it reaches the outlet check valve chamber, entering through passageway 222. Since the outlet check valve diaphragm opening 144 is unobstructed, fluid is free to pass through the opening 144, into the outlet check valve chamber 134, through the air-in-line detector, flushing out the air and priming the system for operation.

The knob 108 is then turned to activate (depress) the outlet check valve, moving the central disk 174 into contact with the outlet check valve diaphragm and blocking the central opening 144 in the outlet check valve diaphragm 106. The thinned continuous web portion 176 stretches without breaking, permitting movement of the central disk 174 without detachment from the back plate or loss of integrity of outlet check valve. The final position is shown in FIG. 14. The primed, set pump cassette of this invention is then mounted on the motor drive housing in the position shown in FIG. 6, the self-threading motor drive member 74 securely mounted in the drive receptor 146.

The pumping cassette connected to the motor drive is shown in FIG. 14, with the exception that the motor drive housing is not shown. In being mounted in the motor drive housing, the inlet check valve member 152 is depressed by a protruding surface of the housing. The central disk 152 is pressed toward the inlet check valve diaphragm 104, the circular ridge 200 pressing the diaphragm 104 inward and against the raised circular ridge of the valve seat 120. Thus the inlet check valve is activated by the operation of pressing the pumping cassette against a raised portion of the motor drive housing.

It will be readily apparent to a person skilled in the art that the outlet check valve can also be constructed to be activated by a portion of the motor drive housing rather than a separate knob 108, or that the inlet check valve can be constructed to be separately activated by a control knob rather than the motor housing surface, and both of these alternative embodiments are included within this invention. However, the embodiment shown in FIG. 13 and 14 is the preferred embodiment. After pumping is terminated, the pumping cassette can be disconnected from the motor drive and removed from the motor drive housing. The inlet check valve will be inactivated to the open position upon return of the inlet check valve elements to the initial priming position shown in FIG. 13. The knob 108 can be rotated to a position which establishes the desired gravity flow rate, assuming the fluid source is positioned at a higher elevation than the patient and cassette.

FIG. 15 is a partial cross-sectional view of the installed cassette assembly of FIG. 13 during the output phase of the pumping cycle, and FIG. 16 shows the installed cassette assembly during the filling phase of the pumping cycle. During the output phase, the motor drive element 74 advances toward the pumping cassette, moving the face 212 of the central diaphragm segment 158 toward the opposing face of the pump chamber cavity, thus reducing the volume of the pumping chamber. This movement is permitted by the flexure (with some stretching) of the hinge segments 164, 166, 168 and 170 and the corresponding movement of the rigid plate segments 160 and 162. The combination of the rigid plate segments and small area of the hinges provides prevents any significant distortion of the pumping chamber volume due to flexure of the pumping surfaces in the manner of resilient pump diaphragms. The pump of this invention thus combines the unique features of a diaphragm pump with the precision of a piston pump. With the pump configuration of this invention, an output volume which is a function of the pumping displacement is achieved, permitting the control precision of a piston pump with the simple construction and energy efficiency of a diaphragm pump.

The fluid expressed from the pumping chamber is expelled through the outlet passageway 252 and eventually to the outlet check valve. The fluid pressure between the element 174 and the outlet check valve diaphragm 106 displaces the diaphragm surface from the surface of the element 174, exposing the diaphragm 60 passageway 144. Liquid passes through opening 144 and cavity 134 to the air-in-line detector inlet 90. Reverse flow of liquid to the source is prevented by the construction of the inlet check valve. The volume 151 defined by the surface of the actuator 152, the ridge 200 and the inlet check valve diaphragm 104 is in direct communication with the pumping chamber, and the increased pressure of the output phase of the pump presses the diaphragm 104 securely against the seat 120, preventing fluid escape to the inlet passageway.

The back pressure in the system downstream of the pumping chamber, for example in the case of occlusion of a parenteral solution infusion needle, is transmitted by drive element 74. This increases the flexure of the flexible beam 6 (FIG. 4 and 5) and is reflected in the changes in capacitance between the capacitor plates 32 and 34.

The reverse flow of the filling phase of the pump is shown in FIG. 16. Reverse motion of the pump element 74 pulls the central rigid diaphragm segment 158 away from the opposing surface of the front plate, increasing the volume of the pumping chamber. The rigid, hinged plates 160 and 162 follow, the plate structure bending about the hinges 164, 166, 168 and 170. The rigid plate construction again achieves a volume change which is a direct function of the displacement of the actuator 74, achieving a precise filling volume. The volume is not affected significantly by the difference in pump chamber pressure and atmospheric pressure.

The pressure in the pumping chamber and chamber 151 during the filling phase falls below the relative pressure in the inlet conduit 82 and inlet check valve inlet 116. The inlet fluid pressure displaces the face of the inlet check valve diaphragm 104 away from the valve seat 120, permitting liquid flow through the inlet check valve to the passageway 204 and to the pumping chamber. The pressure in the outlet chamber 134. exceeds the pressure in the pumping chamber during the filling phase, pressing the outlet check valve diaphragm 106 firmly against the surface of the outlet check valve element 174. Reverse flow of liquid from the outlet chamber 134 during the filling phase is thus prevented.

The outlet check valve assembly provides an additional safety feature. If the cassette 77 becomes dislodged from the housing 79, the outlet check valve actuator 174 remains in the forward position, pressing against the disk 106 and preventing any further fluid flow to the patient.

It will be readily apparent to a person skilled in the art that the back pressure sensor of this invention can be used with any positive displacement pump, and can be connected with the movable pumping actuator member in a variety of ways. A connection which is suitable for a piston pump or diaphragm pump may not be suitable for use with a syringe pump or peristaltic pump, for example. All suitable connections wherein the back pressure sensor system of this invention can be used are intended to be included within the invention.

Likewise, while the relative positions of the flexible and sensor beams and capacitor plates has been described such that the flexible and sensor beams are parallel and the increasing back pressure flexes the flexible beam away from the sensor beam, increasing the spacing between the capacitor plates, it will be readily apparent to a person skilled in the art that alternative and even opposite configurations can be devised within the scope of this invention. For example, the flexible and sensor beams can be initially positioned at an angle to each other, and increasing pump pressure can cause the flexible beam to approach an orientation more parallel with the sensor beam. The distance between the capacitor plates can be thus designed to decrease with increasing pump back pressure. All such variations in the relationship between the flexible and sensor beams are intended to be included within the scope of this invention.

We claim:

1. A back pressure sensor comprising a flexible beam having a pivot end and a drive connector end, the pivot end thereof having a pivot means, a pump actuator means joined to the flexible beam at a position intermediate the pivot end and drive connector end for connecting to a positive displacement member of a pump, a sensor beam attached to the flexible beam at a connecting position spaced from said pivot means, a first capacitor plate mounted on the flexible beam at a plate position which is spaced from the connecting position, a second capacitor plate mounted on the sensor beam in a position facing and spaced apart from the first capacitor plate at a distance which permits formation of a capacitance coupling between the first and second capacitor plates.

2. The back pressure sensor of claim 1 wherein the initial, unstressed positions of the sensor beam and flexible beam are substantially parallel.

3. The back pressure sensor of claim 2 wherein the first capacitor plate is mounted at the pivot end of the flexible beam and the second capacitor plate is mounted at the end of the sensor beam adjacent the pivot end of the flexible beam.

4. The back pressure sensor of claim 1 wherein the sensor beam is connected to the flexible beam at a position adjacent the drive connector end thereof.

5. A pump-pressure sensor combination of a positive displacement pump and the pressure sensor of claim 1 comprising a pumping chamber for containing liquid to pumped, a positive displacement member means for expelling liquid from the pumping chamber, the positive displacement member means connecting with said pump actuator means, whereby increasing pressure in the pumping chamber effects an increasing flexure of the flexible beam and changes the distance between the capacitor plates.

6. The pump-pressure sensor combination of claim 5, wherein the initial unstressed positions of the sensor beam and the flexible beam are substantially parallel.

7. The pump-pressure sensor combination of claim 6 wherein the first capacitor plate is mounted on the pivot end of the flexible beam and the second capacitor plate is mounted on the end of the sensor beam adjacent the pivot end of the flexible beam.

8. The pump-pressure sensor combination of claim 5 wherein the sensor beam is connected to the flexible beam at a position adjacent the drive connector end thereof.

9. The pump-pressure sensor combination of claim 5 wherein the pump is a diaphragm pump comprising a first plate having a pumping chamber surface, a second plate attached to the first plate around the periphery thereof, the second plate comprising a flexible diaphragm member comprising hinged, rigid plates hingingly mounted on the second plate and opposed to the pumping chamber surface to form a pumping chamber, and a check valve means defined by the first and second plates and communicating with the pumping chamber.

10. The pump-pressure sensor combination of claim 9 wherein the flexible diaphragm member comprises at least three inflexible diaphragm plates with edges in a common plane, each diaphragm plate having at least two straight diaphragm plate hinge edges, each diaphragm plate hinge edge being adjacent to and aligned with a second diaphragm plate hinge edge of an adjacent diaphragm plate, the adjacent edges of each diaphragm plate hinge edge and second diaphragm plate hinge edge being attached together by a flexible hinge strip.

11. The pump-pressure sensor combination of claim 10 wherein the first array of plates comprises at least three identical plates having identical edges, the respective identical edges thereof being positioned equal distant from the axial center of symmetry.

12. The pump-pressure sensor combination of claim 11 wherein the flexible member includes a central plate, the axial center of the center plate being at the axial center of symmetry, the center plate having straight plate edges having the same length, and the plates include an array of plates hingingly connected to the straight sides of the center plate, each plate in the array of plates having a straight center plate hinge edge positioned adjacent to and aligned with a center plate edge and hingingly connected at the center plate edge by a flexible hinge strip.

13. The pump-pressure sensor combination of claim 9 wherein the check valve means is a check valve comprising a circular check valve plate attached to the back plate by a flexible hinge means.

14. The pump-pressure sensor combination of claim 13 including an adjustment means threadingly engaging the back plate and having a surface opposing the check valve plate for pressing the check valve plate toward the front plate.

15. The pump-pressure sensor combination of claim 13 wherein the check valve means is an inlet check valve comprising an inlet check valve plate, a valve seat means opposing the check valve plate, and a flexible diaphragm disk with a central flow passageway between the inlet check valve plate and the valve seat means.

16. The pump-pressure sensor combination of claim 15 wherein the flexible inlet diaphragm disk has an inlet side facing the valve seat and communicating with a fluid inlet, and an outlet side facing the inlet check valve plate and communicating with the pumping chamber, the inlet check valve plate being a check valve activation member which by pressing the flexible inlet diaphragm disk against the valve seat means, activates the inlet check valve.

17. The pump-pressure sensor combination of claim 13 wherein the check valve means is an outlet check valve comprising an outlet check value plate including a valve seat means, an outlet check valve chamber opposing the valve seat means, and a flexible outlet diaphragm disk with a central flow passageway between the outlet check valve plate and the outlet check valve chamber.

18. The pump-pressure sensor combination of claim 17 wherein the flexible outlet diaphragm disk has an inlet face facing the valve seat means and communicating with the pumping chamber and an outlet face facing the outlet check value chamber and communicating with a fluid outlet, the outlet check valve plate being a check valve activation member which by pressing the valve seat means against the flexible outlet diaphragm disk, activates the outlet check valve.

19. The pump-pressure sensor combination of claim 18 including an adjustment means threadingly engaging the back plate and having a surface opposing the outlet check valve plate for pressing the outlet check valve plate toward the flexible outlet diaphragm disk for engagement of the valve seat means with the outlet diaphragm disk.

* * * * *